United States Patent [19]

Das

[11] Patent Number: 4,774,239

[45] Date of Patent: Sep. 27, 1988

[54] BENZAZEPINE DERIVATIVES

[75] Inventor: Jagabandhu Das, Hamilton Square, N.J.

[73] Assignee: E. R. Squibb & Sons, Inc., Princeton, N.J.

[21] Appl. No.: 89,479

[22] Filed: Aug. 26, 1987

[51] Int. Cl.$^4$ .................. A61K 31/55; C07D 401/04; C07D 401/06; C07D 401/14; C07D 403/04; C07D 403/06; C07D 403/14; C07D 413/04; C07D 413/06; C07D 413/14; C07D 417/04; C07D 417/06; C07D 417/14

[52] U.S. Cl. ..................................... 514/213; 540/523

[58] Field of Search ..................... 540/523; 514/213

[56] References Cited

U.S. PATENT DOCUMENTS

| | | | |
|---|---|---|---|
| 3,312,691 | 4/1987 | Wertner et al. | 540/523 |
| 3,330,823 | 7/1967 | Bernstein et al. | 540/461 |
| 3,562,257 | 2/1971 | Kugita et al. | 540/491 |
| 3,748,321 | 7/1973 | Krapcho | 540/455 |

OTHER PUBLICATIONS

Chemical Abstracts, vol. 106 (1987), Abstracting European Patent Application EP205,334, published Dec. 17, 1986.
Reaction of 3-Phenylglycidic Esters IV$^1$, Reaction of Methyl 3-(4-Methoxyphenyl)Glycidate With 2-Nitrophenol and Synthesis of 1,5-Benzoxazenine Derivatives, Hashiyama, et al. (Chem. Pharm. Bull.).

Primary Examiner—Robert T. Bond
Attorney, Agent, or Firm—Lawrence S. Levinson; Theodore R. Furman, Jr.

[57] ABSTRACT

A new class of benzazepine derivatives having the general formula

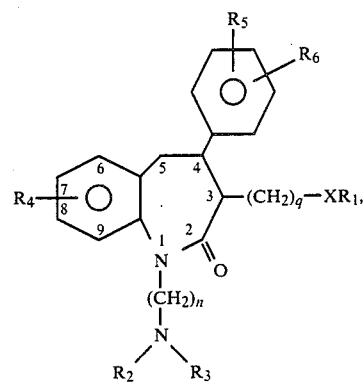

including pharmaceutically acceptable salts, are disclosed. These compounds are useful as cardiovascular agents, particularly as vasodilators.

12 Claims, No Drawings

BENZAZEPINE DERIVATIVES

FIELD OF THE INVENTION

The present invention relates to benzazepine derivatives and more particularly concerns such compounds useful as cardiovascular agents.

SUMMARY OF THE INVENTION

In accordance with the present invention a novel class of benzazepine derivatives useful, for example, as cardiovascular agents, are disclosed. These compounds have the general formula

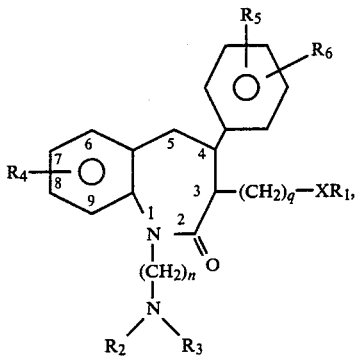

including pharmaceutically acceptable salts thereof, wherein $R_1$ is hydrogen, alkyl, acetyl, aryl, arylalkyl, or $-NR_7R_8$;

X is oxygen or sulfur, or, is a single bond when $R_1$ is $-NR_7R_8$;

$R_2$ and $R_3$ are each independently hydrogen, alkyl, cycloalkyl or arylalkyl, or $R_2$ and $R_3$ together with the nitrogen atom to which they are attached are pyrrolidinyl, piperidinyl, or morpholinyl;

$R_4$, $R_5$, and $R_6$ are each independently hydrogen, halogen, alkyl, alkoxy, aryloxy, arylalkoxy, diarylalkoxy, arylalkyl, cyano, hydroxy, alkanoyloxy,

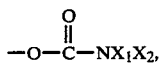

fluoro substituted alkoxy, fluoro substituted alkyl, (cycloalkyl)alkoxy, $-NO_2$, $-NX_3X_4$, $-S(O)_m$alkyl, fluoro substituted alkyl, (cycloalkyl)alkoxy, $-NO_2$, $-NX_3X_4$, $-S(O)_m$alkyl, $-S(O)_m$aryl,

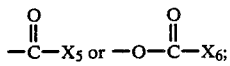

$R_7$ and $R_8$ are each independently hydrogen, alkyl, cycloalkyl or arylalkyl, or $R_7$ and $R_8$ together with the nitrogen atom to which they are attached are pyrrolidinyl, piperidinyl or morpholinyl;

n is 2 or 3;
m is 0, 1 or 2;
q is an integer from 1 to 5;

$X_1$ and $X_2$ are each independently hydrogen, alkyl, aryl or heteroaryl, or $X_1$ and $X_2$ together with the nitrogen atom to which they are attached are pyrrolidinyl, piperidinyl or morpholinyl;

$X_3$ and $X_4$ are each independently hydrogen, alkyl, alkanoyl, arylcarbonyl, heteroarylcarbonyl, or

$X_5$ is hydroxy, alkoxy, aryloxy, amino, alkylamino or dialkylamino; and $X_6$ is alkyl, alkoxy or aryloxy; with the proviso that if $R_4$ is a 7-alkyl group, it must have a tertiary carbon atom bonded to the ring.

DETAILED DESCRIPTION OF THE INVENTION

Listed below are definitions of various terms used to describe the benzazepines of this invention. These definitions apply to the terms as they are used throughout the specification (unless they are otherwise limited in specific instances) either individually or as part of a larger group.

The terms "alkyl" and "alkoxy" refer to both straight and branched chain groups. Those groups having 1 to 10 carbon atoms are preferred.

The term "alkenyl" refers to both straight and branched chain groups. Those groups having 2 to 10 carbon atoms are preferred.

The term "aryl" refers to phenyl and substituted phenyl. Exemplary substituted phenyl groups are phenyl groups substituted with 1, 2 or 3 amino ($-NH_2$), alkylamino, dialkylamino, nitro, halogen, hydroxyl, trifluoromethyl, alkyl (of 1 to 4 carbon atoms), alkoxy (of 1 to 4 carbon atoms), alkanoyloxy, carbamoyl, or carboxyl groups.

The term "alkanoyl" refers to groups having the formula

Those alkanoyl groups having 2 to 11 carbon atoms are preferred.

The term "heteroaryl" refers to an aromatic heterocyclic group having at least one heteroatom in the ring. Preferred groups are pyridinyl, pyrolyl, imidazolyl, furyl, thienyl, or thiazolyl.

The term "cycloalkyl" refers to groups having 3, 4, 5, 6 or 7 carbon atoms.

The term "halogen" refers to fluorine, chlorine, bromine and iodine.

The terms "fluoro substituted alkyl" and "fluoro substituted alkoxy" refer to alkyl and alkoxy groups (as described above) in which one or more hydrogens have been replaced by fluorine atoms. Exemplary groups are trifluoromethyl, 2,2,2-trifluoroethyl, pentafluoroethyl, fluoromethoxy, difluoromethoxy, etc.

The compounds of formula I form acid-addition salts with inorganic and organic acids. These acid-addition salts frequently provide useful means for isolating the products from reaction mixtures by forming the salt in a medium in which it is insoluble. The free base may then be obtained by neutralization, e.g., with a base such as sodium hydroxide. Any other salt may then be formed from the free base and the appropriate inorganic or organic acid. Illustrative are the hydrohalides, especially the hydrochloride and hydrobromide, sulfate, nitrate, phosphate, borate, acetate, tartrate, maleate, citrate, succinate, benzoate, ascorbate, salicylate, methanesulfonate, benzenesulfonate, toluenesulfonate and the like.

The carbon atoms in the 3 and 4-positions of the benzazepine nucleus of the compound of formula I are asymmetric carbons. The compounds of formula I, therefore, exist in enantiomeric and diastereomeric forms and as racemic mixtures thereof. All are within the scope of this invention. It is believed that those compounds of formula I which have the 4R-cis configuration are the most potent and are therefore preferred.

The compounds of formula I can be prepared by first reacting a 2-nitrotoluene having the formula

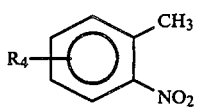
II with a benzylidine malonate having the formula

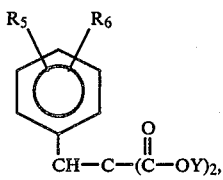
III wherein Y is alkyl. The reaction can be run in a polar nonprotic solvent (e.g., dimethylformamide), in the presence of a strong base such as sodium hydride, and yields a product having the formula

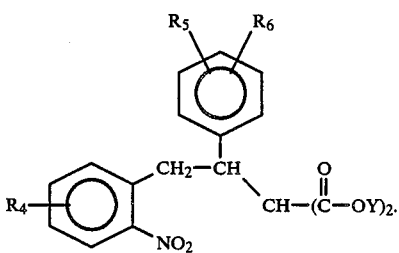
IV

Reduction of a compound of formula IV yields the corresponding compound having the formula

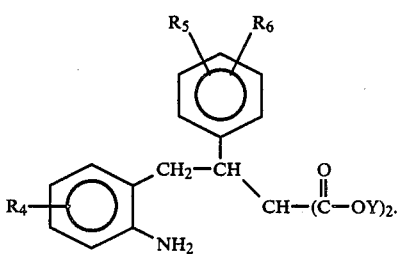
V

The reduction can be accomplished by catalytic hydrogenation (using, for example, palladium on charcoal as a catalyst) or using a chemical reducing agent (e.g., ferrous sulfate or stannous chloride).

Treatment of an amine of formula V with an alkali metal alkoxide (e.g., sodium methoxide) and an alcohol (e.g., methanol) or with potassium hexamethyldisilazide in a solvent such as tetrahydrofuran or toluene, yields the corresponding benzazepine having the formula

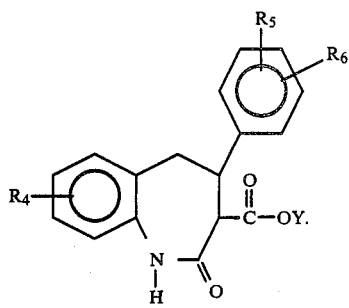
VI

Reaction of a compound of formula VI with a reducing agent, such as lithium aluminum hydride, in a solvent such as tetrahydrofuran, at low temperature yields the corresponding compound having the formula

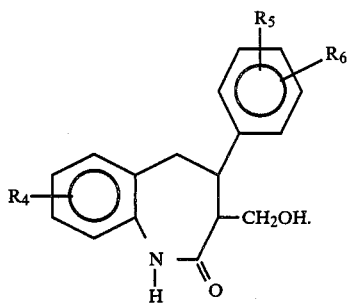
VII

Compound VII can thereafter be reacted with p-toluenesulfonylchloride or methanesulfonylchloride in the presence of a base, such as pyridine to provide a compound having the formula

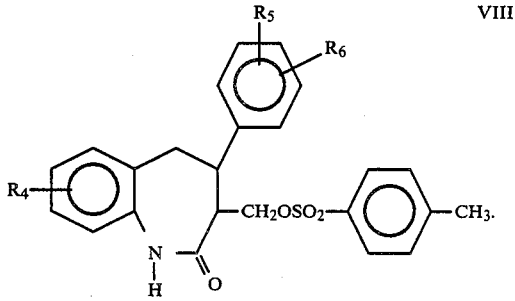
VIII

Compound VIII can be reacted with a base in the presence of a solvent, such as dichloromethane or dimethylformamide, at room temperature, to provide the corresponding compound having the formula

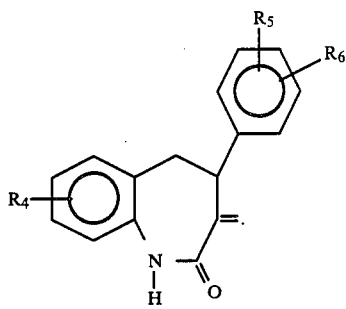

Reaction of a compound of formula IX with a compound of the formula

M—XR$_1$  X where M is a metal, such as lithium, sodium or potassium and X is sulfur or oxygen (such as sodiomethanethiol, where X is sulfur and R$_1$ is methyl; or, sodium methoxide where X is oxygen and R$_1$ is methyl) in the presence of a solvent, such as methanol or dimethylformamide, yields the corresponding compound of the formula

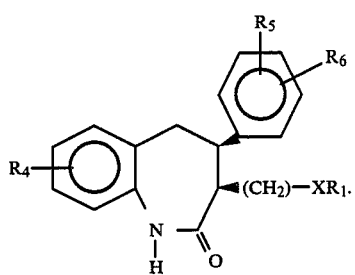

and its diastereomer

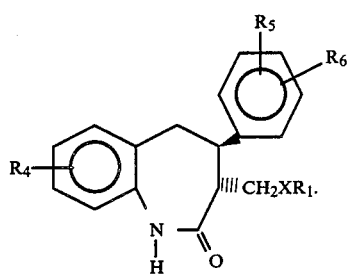

The preferred cis isomer (XIa) is generally the predominant isomer formed during the above reaction. The isomers can be separated using art recognized techniques, such as crystallization or chromatography. Alternatively, the reactions described hereinafter can be carried out using the diastereomeric mixture (a mixture of the compounds of formulas XIa and XIb). The isomeric mixture can be separated into its component isomers at any point during the reaction sequence.

Treatment of a compound of formula XIa with a base, e.g. potassium hydrogen carbonate, in the presence of a solvent, e.g. methyl ethyl ketone, followed by reaction with a compound having the formula

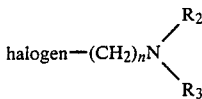

yields the compounds of formula I wherein X is oxygen or sulfur and q is 1.

To prepare compounds of formula I where X is a single bond, q is 1 and R is NR$_7$NR$_8$, a compound of formula IX is treated with an amine of formula

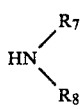

in a solvent like toluene to obtain a diastereomeric mixture of compounds of formulas

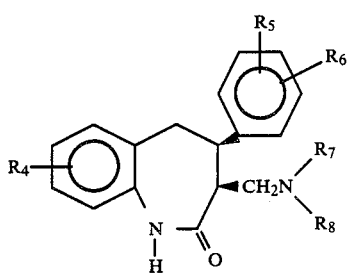

and

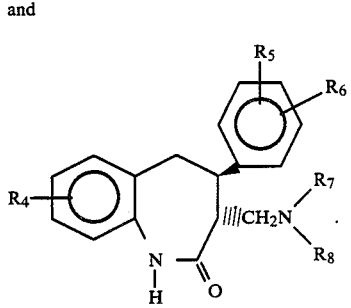

The diastereomers can be separated at this stage using art recognized techniques such as crystallization or chromatography. A compound of formula XIIIa can be treated as a compound of formula XIa to provide a compound of formula I where X is a single bond, q is 1 and R$_1$ is NR$_7$R$_8$. Alternatively, the reaction described above can be carried out using the diastereomeric mixture (a mixture of the compounds of formulas XIIIa and XIIIb). The isomeric mixture can be separated into its component isomers using art recognized techniques, such as crystallization or chromatography.

To prepare compounds of formula I where q is 2 to 5 and X is oxygen or sulfur or X is a single bond and R$_1$ is

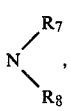

a compound of formula VI in a solvent, e.g., dimethylformamide, in the presence of a base, e.g., sodium hydride is treated with bromomethylmethyl ether to provide a compound having the formula

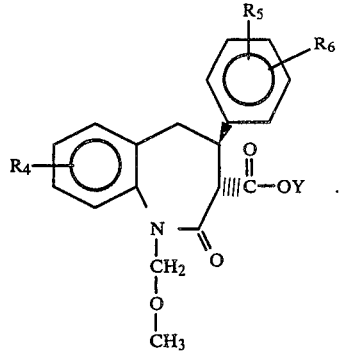

XIV

Compound XIV can be reacted with a compound having the formula $$Br—(CH_2)_{q-1}CH=CH_2 \quad\quad XV$$

in a solvent, e.g., sodium hydride, at low temperature to provide a compound having the formula

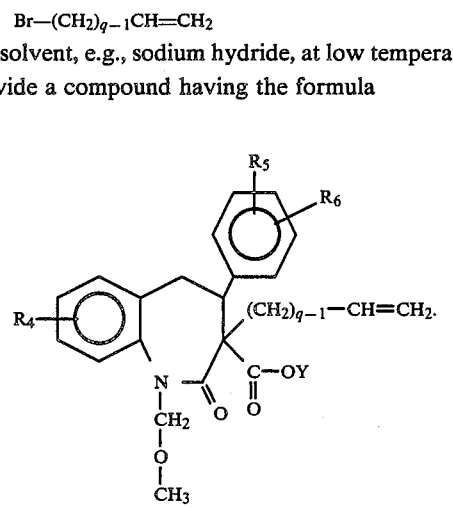

XVI

Treatment of a compound of formula XVI with a strong acid, e.g., sulfuric, in the presence of a solvent, e.g. methanol and anhydrous lithium bromide, provides

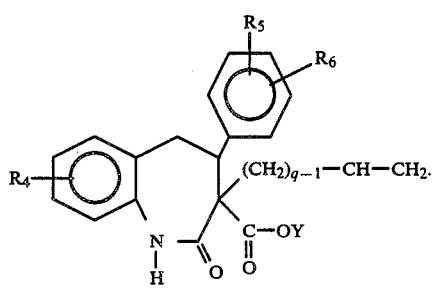

XVII

Compound XVII in a solvent, e.g., pyridine cotaining 1-2% water or dimethylformamide, can therafter be reacted with lithium bromide, or lithium iodide (in presence or absence of p-amino-thiophenol) to obtain a diastereomeric mixture of compounds of formulas

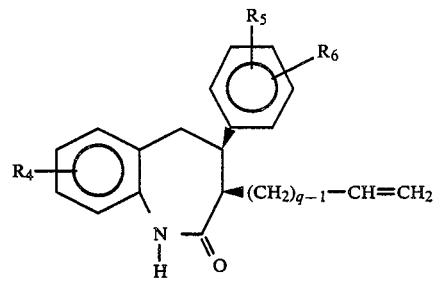

XVIIIa and

XVIIIb

The preferred cis isomer is generally the predominant isomer formed during the above reaction. The isomers can be separated at this stage using art recognized techniques, such as crystallization or chromatography. Alternatively, the reactions described hereinafter can be carried out using the diastereomeric mixture (mixture of compounds of formulas XVIIIa and XVIIIb). The isomeric mixtures can be separated into its component isomers at any point during the reaction sequence using art recognized techniques, such as crystallization of chromatography.

Reaction of the compound of formula XVIIIa in a solvent such as tetrahydrofuran with an ethereal solution of osmium tetroxide followed by treatment with aqueous sodium bisulfite solution provides a compound of the formula

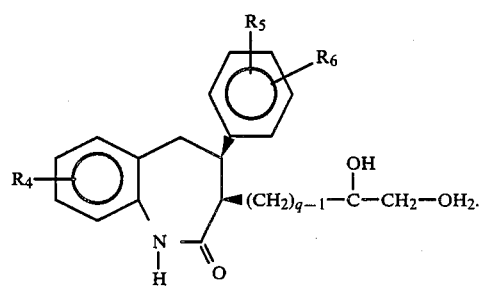

XIX

Treatment of compound XIX in methanol with sodium-meta-periodate in water provides a compound of the formula

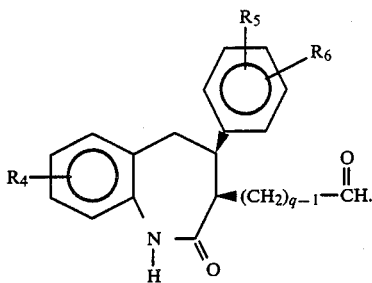

XX

Compound XX, in an organic solvent such as tetrahydrofuran can be reacted with a reducing agent such as sodium borohydride or lithium aluminum hydride to provide a compound of the formula

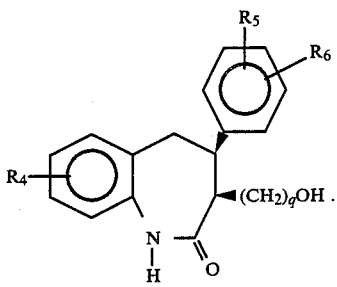

XXI

The compound of formula XXI can be acylated or alkylated using a conventional techniques to obtain products of formula

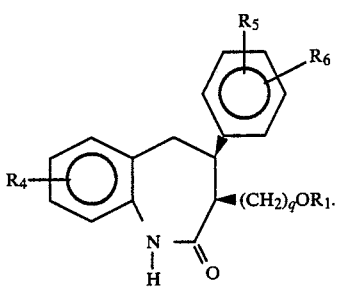

XXII

For example, Compound XXI can be reacted with a halide of the formula $R_1$—halogen  XXIII in the presence of a base. Alternatively, the acylation can be accomplished using an acid anhydride.

Treatment of a compound of formula XXII with an alkali metal hydride (e.g., sodium hydride) in an inert solvent, such as dimethylformamide or dimethylsulfoxide, followed by reaction with a compound of formula XII yields the compound of formula I, wherein X is oxygen and $R_1$ is acetyl, alkyl, aryl or arylalkyl. Alternatively, compounds of formula XXII, in the presence of a base like potassium hydrogen carbonate can be treated with compounds of formula XII in a solvent, e.g., methyl ethyl ketone, to provide compounds of formula I, where —$XR_1$ is —$OR_1$ and q is 2 to 5.

To prepare compounds of formula I, where q is 2 to 5 and —$XR_1$ is —$SR_1$ or

a compound of formula XXI, in a solvent, e.g., tetrahydrofuran, can be reacted with triphenylphosphine and diisopropyl azodicarboxylate, followed by $HSR_1$ or

to provide compounds of formula

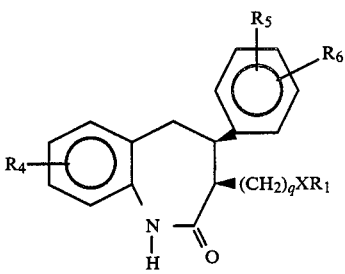

XXIV where $XR_1$=—$SR_1$ or

A compound of formula XXIV can be treated as compounds of formula XXII to provide compounds of formula I, where q is 2 to 5 and —$XR_1$ is either —$SR_1$ or

The resolved enantiomers of the compounds of this invention can be prepared by first hydrolyzing a compound of formula VI to obtain the corresponding carboxylic acid having the formula

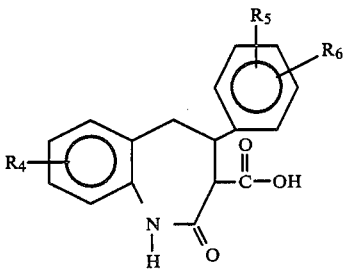

XXV

The hydrolysis can be accomplished, for example, by treating a compound of formula VI with an alkali metal hydroxide in an alcohol (e.g., potassium hydroxide in methanol).

A carboxylic acid of formula XXV can be resolved using a chiral amine. Reaction of the acid and amine in an appropriate solvent yields the diastereomeric salts which can be separated using conventional techniques such as crystallization. Regeneration of the carboxylic acid from the pure diastereomeric salt followed by esterification yields the desired nonracemic form of a compound of formula VI. Alternatively, compounds of formula VI can be generated directly from the diastereomeric salts by treatment with an alkyl halide in dimethylformamide in the presence of an inorganic base (e.g., potassium bicarbonate). This nonracemic compound can be converted to the corresponding nonracemic product of formula I via the nonracemic form of intermediates of formulas VII and VIII using the procedures described above.

Alternatively, the resolved enantiomers of the compounds of this invention can be prepared by the reaction of a compound of formula I with a chiral carboxylic acid in an appropriate solvent. The resulting diastereomeric salts can be separated by recrystallization.

In the reactions described above for preparing the compounds of this invention, it may be necessary to protect reactive substituents (e.g., hydroxy and amino) from involvement in the reactions. Protection of the substituents, and the necessary deprotection, can be accomplished using standard techniques.

Preferred are those compounds of formula I wherein $R_1$ is methyl when X is oxygen or sulfur; $R_1$ is

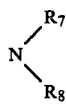

when X is a single bond;

$R_2$ and $R_3$ are each methyl or $R_2$ is hydrogen and $R_3$ is methyl;

$R_4$ is trifluoromethyl (especially 7-trifluoromethyl and 6-trifluoromethyl);

$R_5$ is 4-methoxy;

$R_6$ is hydrogen;

$R_7$ and $R_8$ are each methyl; and, q is 1 or 2.

The compounds of formula I and the pharmaceutically acceptable salts thereof are useful as cardiovascular agents. These compounds act as vasodilators and are especially useful as anti-hypetensive and anti-ischemic agents. By the administration of a composition containing one (or a combination) of the compounds of this invention the blood pressure of a hypertensive mammalian (e.g. human) host is reduced. Daily doses of about 0.1 to 100 mg per kilogram of body weight per day, preferably about 1 to about 50 mg per kilogram per day, are appropriate to reduce blood pressure, and can be administered in single or divided doses. The substance is preferably administered orally, but parenteral routes such as the subcutaneous, intramuscular, or intravenous routes can also be employed.

As a result of the vasodilating activity of the compounds of formula I, it is believed that such compounds in addition to being anti-hypertensives may also be useful as anti-arrhythmic agents, as anti-anginal agents, as anti-fibrillatory agents, as anti-asthmatic agents, and in limiting myocardial infarction.

The compounds of this invention can also be formulated in combination with a diuretic or an angiotensin converting enzyme inhibitor. Suitable diuretics include the thiazide diuretics such as hydrochlorothiazide and bendroflumethiazide and suitable angiotensin converting enzyme inhibitors include captopril.

The present invention will be further described by reference to the following examples, however, it is not meant to be limited by the details described therein.

EXAMPLE 1

(cis)-1-[2-(Dimethylamino)ethyl]-1,3,4,5-tetrahydro-3-(methoxymethyl)-4-(4-methoxyphenyl)-7-(trifluoromethyl)-2H-1-benzazepin-2-one, fumarate (1:1) salt

A.

[2-(5-Trifluoromethyl-2-nitrophenyl)-1-(4-methoxyphenyl)ethyl]propanedioic acid, dimethyl ester To a 2 liter three-neck flask (under nitrogen) was added 67.0 g (0.293 mole) of dimethyl-p-methoxybenzylidene malonate and 450 ml of dimethylformamide. The stirred solution was treated with a 50% sodium hydride dispersion (18.7 g, 0.39 mol). The mixture was treated dropwise with a solution of 3-methyl-4-nitrobenzoic acid (60.5 g, 0.293 mol) in 50 ml of dimethylformamide over a period of 1 hour while maintaining a temperature at about 28°–32° C. This mixture was stirred for 4 hours at room temperature, cooled, treated portionwise with 25 ml of acetic acid and poured onto 2.5 l of ice-water. The mixture was extracted 3 times with 250 ml of methylene chloride. The organic phases were combined, washed 3 times with 500 ml of water, dried over magnesium sulfate, filtered and the solvent evaporated to give 126 g of a pale brown semi-solid. The latter was dissolved in 270 ml of methanol, cooled and filtered to give 72.8 g of a pale yellow product, m.p. 110°–112°. A sample recrystallized from methanol, melted at 111°–113°.

Analysis calc'd for $C_{21}H_{20}NF_3O_7$: C, 55.39, H, 4.43, N, 3.08; F, 12.52; Found: C, 56.08; H, 4.70; N, 2.96; F, 12.09.

B.

[2-(5-Trifluoromethyl-2-aminophenyl)-1-(4-methoxyphenyl)ethyl]propanedioic acid, dimethyl ester A suspension of 25 g (0.055 mol) of the title A compound in 200 ml of methanol was treated with a cold suspension of 2.5 g of 5% palladium on carbon in 50 ml of methanol (under nitrogen) and placed on the Parr apparatus at 58 psi of hydrogen. After 30 minutes, this mixture was heated to 50°–55° C. for 1 hour to assure that all of the nitro compound had dissolved. The mixture was removed from the Parr and allowed to stand at room temperature overnight. The flask was heated to dissolve the crystallized product and the hot solution was filtered through Celite (under nitrogen) and washed with hot methanol. The colorless filtrate was concentrated on a rotary evaporator to give 22.2 g of a nearly colorless solid. The latter was triturated with 100 ml of hexane and then with 50 ml of hexane. The solvent was decanted and the entrained solvent removed on a rotary evaporator to give 21.3 g of product, m.p. 124°–127°. A sample of this material, after crystallization from methanol, melted at 125°–127 °.

Analysis calc'd for $C_{21}H_{22}NF_3O_5$: C, 59.29; H, 5.21; N, 3.29; F, 13.40; Found: C, 59.48; H, 5.26; N, 3.16; F, 13.43.

C.

7-(Trifluoromethyl)-1,3,4,5-tetrahydro-3-(methoxycarbonyl)-4-(4-methoxyphenyl)-2H-1-benzazepin-2-one A stirred solution of the title B compound (20.0 g, 0.047 mol) in 200 ml of methanol was treated with 13.3 ml of 25% sodium methoxide in methanol and heated to reflux. After 2.75 hours, the mixture was cooled in ice water and 70 ml of 1N hydrochloric acid was added to precipitate the partly gummy product. The latter became granular on rubbing and stirring in an ice water bath for 0.5 hours. The tan solid was filtered, washed with water, and air dried to give 19 g of a pale yellow foam-like material. The latter was suspended in 30 ml of isopropylalcohol, allowed to stand for 1 hour, filtered and washed with isopropylalcohol and hexane to provide 13.64 g of the title C compound, m.p. 161°–163°.

Analysis calc'd for $C_{20}H_{18}NF_3O_4$: C, 61.07; H, 4.61; N, 3.56; F, 14.49; Found: C, 61.26; H, 4.62; N, 3.41; F, 14.21.

D.

7-(Trifluoromethyl)-1,3,4,5-tetrahydro-3-(hydroxymethyl)-4-(4-methoxyphenyl)-2H-1-benzazepin-2-one The title C compound (29.16 g, 74.13 mmole) in dry tetrahydrofuran (150 ml) was added dropwise and with stirring to a cooled (0° C.) solution of lithium aluminum hydride (6.41 g, 0.169 mole) in tetrahydrofuran (50 ml). The ice bath was removed and the solution was stirred at room temperature for 4 hours. Saturated sodium sulfate solution was carefully added to neutralize the hydride and the mixture was partitioned between water and ethyl acetate. The organic extract was dried over anhydrous magnesium sulfate, filtered and concentrated. The crude residue was digested in hot isopropyl ether and the precipitated title D compound (10.93 g) was collected by suction-filtration (m.p. 189.5°–190.5° C.).

Analysis calc'd for $C_{19}H_{18}NO_3F_3$: C, 62.46; H, 4.97; N, 3.84; F, 15.59; Found: C, 62.70; H, 5.25; N, 3.76; F, 15.61.

E.

7-(Trifluoromethyl)-1,3,4,5-tetrahydro-4-(4-methoxyphenyl)-3-(p-toluenesulfonyloxymethyl)-2H-1-benzazepin-2-one p-Toluene sulfonyl chloride (3.31 g, 17.36 mmole) was added with stirring to a solution of the title D compound (4.2 g, 11.57 mmole) in methylene chloride (75 ml) and pyridine (5 ml). The reaction mixture was stirred at room temperature for 6 hours, whereupon it was diluted with ethyl acetate and washed successively with water, 2N hydrochloric acid solution and water. The aqueous extracts were combined and extracted with ethyl acetate. The combined organic extract was dried over anhydrous magnesium sulfate and concentrated. The yellow residue was dissolved in methylene chloride (10 ml) and isopropyl ether (100 ml), cooled to −20° C. and the white precipitate was filtered to obtain 4.93 g of the title E compound. The mother liquor was concentrated and chromatographed on a silica gel column. Elution with 20–40% ethyl acetate in hexane afforded additional 430 mg of the title E compound for a total yield of 5.36 g, m.p. 170°–172° C.

Analysis calc'd for $C_{26}H_{24}NF_3O_5S$: C, 60.11; H, 4.66; N, 2.70; F, 10.97; S, 6.17; Found: C, 60.21; H, 4.77; N, 2.59; F, 10.92; S, 5.94.

F.

7-(Trifluoromethyl)-1,3,4,5-tetrahydro-4-(4-methoxyphenyl)-3-methylene-2H-1-benzazepin-2-one To the title E compound (9.36 g, 18.0 mmole) in dimethylformamide (30 ml) was added diazabicycloundecene (DBU) (5.38 ml; 36 mmole; 2 eq) with stirring at room temperature. After 5 hours, the mixture was diluted in ethyl ether/ethyl acetate, washed three times with 1N hydrochloric acid, dried over magnesium sulfate and concentrated to give 7.08 g of the title F compound as a white solid, m.p. 181°–183° C.

Analysis calc'd for $C_{19}H_{16}NF_3O_2$: C, 65.70; H, 4.64; N, 4.03; F, 16.41; Found: C, 65.82; H, 4.77; N, 3.99; F, 16.70.

G.

(cis)-7-(Trifluoromethyl)-1,3,4,5-tetrahydro-3-(methoxymethyl)-4-(4-methoxyphenyl)-2H-1-benzazepin-2-one To a solution of 1.4 g of the title F compound (4.06 mmole) in 50 ml methanol was added with stirring 4 ml of a 4.37M solution of sodium methoxide in methanol (18.48 mmole). The suspension of enone went into solution upon addition of sodium methoxide solution. The homogeneous reaction mixture was heated at 60°–65° C. for 4 hours, whereupon it was cooled, diluted with ethyl acetate and thoroughly washed with water. The combined aqueous layer was extracted once with ethyl acetate. The ethyl acetate extract was dried over anhydrous magnesium sulfate, filtered and concentrated under reduced pressure. The residue was diluted with ethyl acetate, filtered over anhydrous magnesium sulfate (to remove some water carried in the ethyl acetate extract with methanol) and concentrated under reduced pressure. The crude residue was diluted with 100 mL ether, cooled to −20° C. overnight and the precipitated cis-methoxymethyladduct (420 mg) was filtered and washed with ether. The mother liquor was concentrated and chromatographed on a silica gel column. Elution with 10–50% ethyl acetate in hexane afforded an additional 153 mg of the title G compound, m.p. 220°–228° C.

Analysis calc'd for $C_{20}H_{20}NF_3O_3 \cdot 0.65H_2O$: C, 61.42; H, 5.49; N, 3.58; F, 14.57; Found: C, 61.31; H, 5.15; N, 3.57; F, 14.94.

H.

(cis)-1-[2-(Dimethylamino)ethyl]-1,3,4,5-tetrahydro-3-(methoxymethyl)-4-(4-methoxyphenyl)-7-(trifluoromethyl)-2H-1-benzazepin-2-one, fumarate (1:1) salt The title G compound (400 mg, 1.05 mmole) was dissolved completely in refluxing methyl ethyl ketone (10 ml) under argon. Potassium hydrogen carbonate (0.42 g, 4.2 mmole, 4 eq) was added to the solution, followed by dimethylformamide (3 ml) while maintaining the oil bath temperature at 85°–90° C. After stirring for 15 minutes, a 2.15M toluene solution of N,N-dimethyl-2-chloroethylamine (0.98 ml, 2.1 mmole) was added and heating was continued for 5 hours. The mixture was cooled, diluted with ethyl acetate, washed with water and sodium hydrogen carbonate, dried over magnesium sulfate and concentrated. The crude free amine material was purified over a silica gel eluting with 10% methanol in methylene chloride to yield 260 mg of pure cis free amine product. This material was dissolved in methanol and treated with an equivalent of fumaric acid to give 320 mg of the title compound, m.p. 152°–157° C.

Analysis calc'd for $C_{28}H_{33}N_2F_3O_7 \cdot 0.32H_2O$: C, 58.76; H, 5.92; N, 4.90; F, 9.96; Found: C, 58.88; H, 5.97; N, 4.86; F, 10.12.

EXAMPLE 2

(cis)-1-[2-(Dimethylamino)ethyl]-1,3,4,5-tetrahydro-4-(4-methoxyphenyl)-3-[(methylthio)methyl]-7-(trifluoromethyl)-2H-1-benzazepin-2-one, fumarate (1:1) salt

A.

7-(Trifluoromethyl)-1,3,4,5-tetrahydro-4-(4-methoxyphenyl)-3-[(methylthio)methyl]-2H-1-benzazepin-2-one To the title F compound of Example 1 (1.00 g, 2.88 mmole) in dimethylformamide (5 ml) was added sodiumthiomethoxide (300 mg, 4.28 mmole, 1.5 eq) with stirring at room temperature under an argon atmosphere. After 15 minutes, the mixture was diluted with ether and washed twice with water, followed by saturated sodium chloride. The ether layer, which contained a white solid emulsion, was suction-filtered and the solid was rinsed twice with ether, and vacuum dried to yield 760 mg of the title A compound, m.p. 224°–226.5° C. (contains 90% cis and 10% trans).

B.

(cis)-1-[2-(Dimethylamino)ethyl]-1,3,4,5-tetrahydro-4-(4-methoxyphenyl)-3-[(methylthio)methyl]-7-(trifluoromethyl)-2H-1-benzazepin-2-one, fumarate (1:1) salt The title A compound (750 mg, 1.9 mmole) was dissolved in refluxing methyl ethyl ketone (20 ml) under argon. Potassium hydrogen carbonate (0.76 g, 7.6 mmole, 4 eq) was added to the solution while maintaining the oil bath temperature at 85°–90° C. After stirring for 15 minutes, a 2.15M toluene solution of N,N-dimethyl-2-chloroethylamine (1.8 ml, 3.8 mmole) was added, and heating was continued for 5 hours. The mixture was cooled, diluted with ethyl acetate, washed with water and 1N sodium hydrogen carbonate, dried over magnesium sulfate, and concentrated. The crude free amine product obtained after workup (960 mg) was crystallized from isopropyl ether/hexane. The pure cis product obtained from crystallization was dissolved in methanol and treated with one equivalent of fumaric acid with stirring and then concentrated and vacuum dried to yield 520 mg of the title compound as a white solid, m.p. 130°–134° C.

Analysis calc'd for $C_{28}H_{33}N_2F_3O_6S$: C, 57.72; H, 5.71; N, 4.81; S, 5.50; F, 9.78; Found: C, 57.71; H, 5.86; N, 4.78; S, 5.47; F, 9.55.

EXAMPLE 3

(cis)-3-[2-(Acetyloxy)ethyl]-1-[2-(dimethylamino)ethyl]-1,3,4,5-tetrahydro-4-(4-methoxyphenyl)-7-(trifluoromethyl)-2H-1-benzazepin-2-one, monohydrochloride

A.

7-(Trifluoromethyl)-1,3,4,5-tetrahydro-3-methoxycarbonyl)-1-(methoxymethyl)-4-(4-methoxyphenyl)-2H-1-benzazepin-2-one To a suspension of sodium hydride (360 mg, 7.5 mmole, 50% in oil dispersion/prewashed with dry ether several times) in dry dimethylformamide (30 ml), cooled at 0°–5° C. was added dropwise a solution of the title C compound of Example 1 (1.9 g, 5 mmole) in dry dimethylformamide (15 ml). The mixture was stirred for an additional 20 minutes at 0°–5° C., whereupon bromomethylmethyl ether (800 μl, 10 mmole) was added dropwise, and stirring was continued at this temperature for another hour. Excess sodium hydride was destroyed by the addition of water. The mixture was diluted with ether and washed with water. The aqueous layer was extracted three times with ethyl ether and the combined organic extracts were dried over magnesium sulfate and concentrated. The crude oily residue was flash chromatographed to obtain 1.67 g of the title A compound as a colorless oil.

B.

3-Allyl-1,3,4,5-tetrahydro-3-(methoxycarbonyl)-1-(methoxymethyl)-4-(4-methoxyphenyl)-7-(trifluoromethyl)-2H-1-benzazepin-2-one To a suspension of sodium hydride (384 mg, 8 mole, 50% in oil dispersion) in dry dimethylformamide (35 ml), cooled in an ice-water bath, was added a solution of the title A compound (917 mg, 21 mmole) in dimethylformamide (8 ml) with stirring. After 30 minutes at 0°–5° C., allylbromide (1.5 ml) was added in one portion. The mixture was allowed to stand at 0°–5° C. for 3 additional hours, whereupon excess hydride was destroyed by the addition of water. The mixture was diluted with ether and washed with water. The aqueous layer was extracted three times with ether, and the combined ethyl ether extracts were dried over magnesium sulfate, and concentrated. The crude residue was flash chromatographed to obtain 905 mg of the title B compound as a white crystalline material.

C.

3-Allyl-1,3,4,5-tetrahydro-3-(methoxycarbonyl)-1-4(methoxyphenyl)-7-(trifluoromethyl)-2H-1-benzazepin-2-one Concentrated sulfuric acid (8 ml) and anhydrous lithium bromide (720 mg, 8 mmole) were added to a suspension of the title B compound (905 mg, 1.9 mmole) in methanol (40 ml) with stirring. The reaction mixture was heated under reflux for 9 hours, and then allowed to stand overnight at room temperature. The acid was carefully neutralized by the addition of saturated sodium hydrogen carbonate solution and the mixture was extracted three times with ethyl acetate. The combined organic extracts were dried over magnesium sulfate and concentrated giving 858 mg of the title C compound as an off-white solid.

D.

(cis)-3-Allyl-1,3,4,5-tetrahydro-4-(methoxyphenyl)-7-(trifluoromethyl)-2H-1-benzazepin-2-one Lithium iodide (53.34 g, 0.4 mole) was added with stirring to a solution of the title C compound (42.94 g, 0.099 mole) in pyridine (300 ml), containing 1–2% water and the mixture was heated under reflux overnight. Most of pyridine was removed by distillation in vacuo. The residue was dissolved in chloroform and washed with 1N hydrochloric acid solution (4×) and saturated brine. The chloroform extract was dried over anhydrous magnesium sulfate and concentrated to obtain a reddish residue, which was triturated with methanol to obtain the pure cis - title D compound (19.87 g) as a white solid.

E.
(cis)-7-(Trifluoromethyl)-1,3,4,5-tetrahydro-3-(2,3-dihydroxypropyl)-4-(4-methoxyphenyl)-2H-1-benzazepin-2-one To a solution of the title D compound (1.86 g, 5 mmol) in distilled tetrahydrofuran (30 ml) was added 200 μl of osmium tetroxide solution (1 g in 10 ml of ether) with stirring. N-methylmorpholineN-oxide (880 mg, 6.5 mmol, 1.3 eq) in 3 ml of water was then added dropwise. The reaction mixture was allowed to stir at room temperature for 8 hours. The mixture was diluted with ethyl acetate and an aqueous sodium bisulfite solution was added. The biphasic reaction mixture was stirred for 10 minutes to reduce the osmate ester. The organic layer was then separated and the aqueous layer was extracted twice with methylene chloride. The combined organic extracts were dried over magnesium sulfate and concentrated giving 1.97 g of the title E compound as a white solid.

F.
(cis)-7-(Trifluoromethyl)-1,3,4,5-tetrahydro-[2-(hydroxy)ethyl]-4-(4-methoxyphenyl)-2H-1-benzazepin-2-one A solution of sodium metaperiodate (2.14 g, 10 mmol) in 10 ml of water was added dropwise with stirring to a solution of the title E compound (1.97 g, 5 mmol) in 30 ml of methanol cooled in an ice-water bath. A white precipitate formed immediately. After stirring for 30 minutes, the mixture was diluted with water and extracted 4 times with ethyl acetate. The combined extracts were dried over magnesium sulfate and concentrated to obtain the white crystalline aldehyde. This material was dissolved in 40 ml of tetrahydrofuran, cooled in an ice-water bath, and a solution of sodium borohydride (190 mg, 5 mmol) in 2 ml of water was added dropwise. The mixture was allowed to stand at 0°–5° C. for 30 minutes, whereupon excess borohydride was destroyed by dropwise addition of 2N hydrochloric acid. The mixture was diluted with ethyl acetate and washed several times with water. The combined aqueous layers were extracted twice with ethyl acetate. The organic extracts were dried over magnesium sulfate and concentrated. This material was flash chromatographed on silica gel yielding 1.43 g of the title F compound.

G.
(cis)-3-[2-(Acetoxy)ethyl]-1,3,4,5-tetrahydro-4-(4-methoxyphenyl)-7-(trifluoromethyl)-2H-1-benzazepin-2-one To a solution of the title F compound (1.1 g, 2.95 mmol) in methylene chloride (15 ml) and 5 ml of pyridine was added 3 ml of acetic anhydride with stirring. After stirring at room temperature for 8 hours, the mixture was diluted with ethyl acetate and washed with saturated copper sulfate solution. The combined copper sulfate extract was extracted twice with ethyl acetate. The combined organic layers were washed with water, dried over magnesium sulfate and concentrated to give an oily residue, which was flash chromatographed on silica gel using 25–50% ethyl acetate/hexane to give 1.1 g of the title G compound as a white solid.

H.
(cis)-3-[2-(Acetyloxy)ethyl]-1-[2-(dimethylamino)ethyl]tetrahydro-4-(4-methoxyphenyl)-7-(trifluoromethyl)-2H-1-benzazepin-2-one, monohydrochloride Potassium iodide (83 mg, 0.50 mmol) and the title G compound (880 mg, 2.09 mmol) were suspended in 20 ml of methyl ethyl ketone. N,N-dimethylaminoethyl chloride (2.15M in toluene, 1.25 ml, 2.69 mmol) was added and the mixture was refluxed for 8 hours. The mixture was concentrated and the residue dissolved in ethyl acetate and washed twice with water. The organic layer was dried over magnesium sulfate and concentrated leaving 980 mg of an oil which was flash chromatographed on silica gel using 0.1–3.0% methanol in methylene chloride. The pure cis-amine (obtained after a second chromatography on silica gel with 0.7–1.5% methanol in methylene chloride as eluents) was treated with etheral hydrogen chloride to obtain 480 mg of title H compound as a white solid, m.p. 206°–207° C.

Analysis calc'd for $C_{26}H_{31}F_3N_2O_4 \cdot HCl$: C, 59.03; H, 6.10; N, 5.30; Cl. 6.70; F, 10.77; Found: C, 58.97; H, 6.11; N, 5.25; Cl, 6.68; F, 10.62.

EXAMPLE 4
(cis)-1-[2-(Dimethylamino)ethyl]-3-[(dimethylamino)methyl]-1,3,4,5-tetrahydro-4-(4-methoxyphenyl)-7-(trifluoromethyl)-2H-1-benzazepin-2-one, fumarate (1:2) salt

A.
(cis)-3-[(Dimethylamino)methyl]-1,3,4,5-tetrahydro-4-(4-methoxyphenyl)-7-(trifluoromethyl)-2H-1-benzazepin-2-one, fumarate (1:1) salt To the title F compound of Example 1 (1 g, 2.88 mmol) in 7 ml of toluene was added 5 ml of a 8.87M solution of dimethylamine in water (44 mmole) and 50 mg of benzyltrimethylammonium chloride. The mixture was heated under reflux with vigorous stirring for 2.5 hours, whereupon it was cooled and diluted with ether. The organic layer was separated, washed with water, dried over anhydrous magnesium sulfate and concentrated. The residue was diluted with ether and the precipitated white solid (750 mg) was filtered off. Crystallization from methanol provided 220 mg of pure cis-amine, which was dissolved in warm methanol and treated with one equivalent of fumaric acid to obtain 270 mg of the title A compound as a white solid, m.p. 166°–167° C.

Analysis calc'd for $C_{25}H_{27}N_2F_3O_6$: C, 59.05; H, 5.35; N, 5.51; F, 11.21; Found: C, 59.01; H, 5.41; N, 5.84; F, 11.34.

B.
(cis)-1-[2-(Dimethylamino)ethyl]-3-[(dimethylamino)methyl]-1,3,4,5-tetrahydro-4-(4-methoxyphenyl)-7-(trifluoromethyl)-2H-1-benzazepin-2-one, fumarate (1:2) salt A solution of the title A free amine (560 mg, 1.43 mmol) in methyl ethyl ketone (10 ml) was treated with potassium hydrogen carbonate (570 mg, 5.7 mmole) and a 2.15M solution of N,N-dimethyl-2-chloroethylamine (1.33 ml, 2.85 mmole). The reaction mixture was heated under reflux for 4.5 hours, cooled and diluted with ethyl acetate and water. The ethyl acetate layer was separated, dried over anhydrous magnesium sulfate and concentrated. The residue (650 mg, mixture of cis and trans-products) was purified on silica gel plates with 15% methanol in methylene chloride to obtain 141 mg of Title B free amine product, which was dissolved in methanol and treated with 71 mg of fumaric acid (0.61 mmole, 2 eq) to provide 210 mg of the title B product as a white solid, m.p. 67°–69° C.

Analysis calc'd for $C_{33}H_{40}N_3F_3O_{10}.2.38H_2O$: C, 53.67; H, 6.11; N, 5.69; F, 7.72; Found: C, 53.85; H, 6.04; N, 5.58; F, 7.81.

EXAMPLES 5–28

Following the procedures described above and as outlined in Examples 1–4, the following additional compounds within the scope of the present invention can be made.

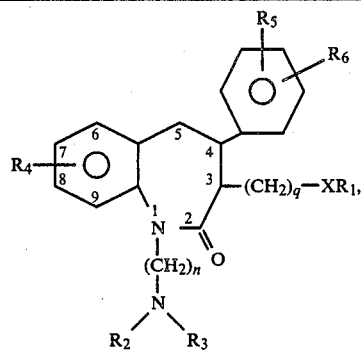

| Ex. No. | X | $R_1$ | $R_2$ | $R_3$ | $R_4$ | $R_5$ | $R_6$ | q |
|---|---|---|---|---|---|---|---|---|
| 5 | S | phenyl | —H | —CH₃ | 7-CF₃ | 4-OCH₃ | H | 1 |
| 6 | S | —CH₂-phenyl | —CH₃ | —CH₃ | 6-CF₃ | 4-OCH₃ | H | 2 |
| 7 | S | —C₂H₅ | —CH₃ | —CH₃ | 6-O—C(=O)—N(pyrrolidine) | 4-OCH₃ | H | 1 |
| 8 | S | —C₃H₇ | —H | —CH₃ | 7-CH₃ | 4-CH₃ | H | 3 |
| 9 | S | —(CH₂)₂-phenyl | | pyrrolidine-N | 7-C₂H₅ | 4-OCH₃ | 3-OCH₃ | 1 |
| 10 | S | —C(=O)—CH₃ | —CH₃ | —CH₂-phenyl | 7-CF₃ | —F | H | 2 |
| 11 | S | phenyl | | —CH₃ | cyclopentyl / 6-CF₃ | 4-OCH₃ | H | 4 |
| 12 | S | —CH₃ | —CH₃ | cyclohexyl | 8-NO₂ | —NO₂ | H | 5 |
| 13 | — | —N(CH₃)₂ | —H | —(CH₂)₂-phenyl | 8-CH₃ | 4-OCH₃ | H | 1 |

-continued

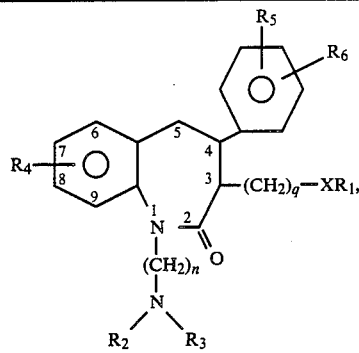

| Ex. No. | X | $R_1$ | $R_2$ | $R_3$ | $R_4$ | $R_5$ | $R_6$ | q |
|---|---|---|---|---|---|---|---|---|
| 14 | — | $-N(CH_3)_2$ | piperidine | | $6-N(CH_3)_2$ | $4-OCH_3$ | H | 2 |
| 15 | O | $-C(O)CH_3$ | morpholine | | $7-N(CH_3)_2$ | $-C_2H_5$ | H | 1 |
| 16 | O | $-C(O)CH_3$ | cyclohexyl | $-H$ | $7-CF_3$ | $-CH_3$ | H | 1 |
| 17 | O | $-C(O)CH_3$ | $-H$ | $-CH_3$ | $7-C(O)OH$ | $-C(O)OH$ | H | 2 |
| 18 | O | $-C(O)CH_3$ | $-CH_3$ | $-CH_3$ | $6-CF_3$ | $-O-C(O)-N(CH_3)_2$ | H | 2 |
| 19 | — | $-N(CH_3)_2$ | $-CH_3$ | cyclohexyl | $7-CF_3$ | $4-OCH_3$ | H | 1 |
| 20 | O | $-CH_3$ | $-H$ | $-H$ | $7-CF_3$ | $4-OCH_3$ | $3-OCH_3$ | 2 |
| 21 | O | $C_2H_5$ | $-C_2H_5$ | $-CH_3$ | $7-CF_3$ | $4-OCH_3$ | H | 1 |
| 22 | — | $-N(CH_2Ph)_2$ | pyrrolidine | | $7-CF_3$ | $4-OCH_3$ | $3-OCH_3$ | 2 |
| 23 | O | $-C(O)CH_3$ | $-H$ | $-CH_3$ | $8-C\equiv N$ | $4-OCH_3$ | H | 1 |
| 24 | O | $-CH_3$ | $-CH_3$ | $-CH_3$ | $8-CH_3$ | $-C\equiv N$ | H | 1 |
| 25 | — | $-N(CH_3)_2$ | $-H$ | $-CH_3$ | $8-CF_3$ | $4-CF_3$ | H | 2 |

-continued

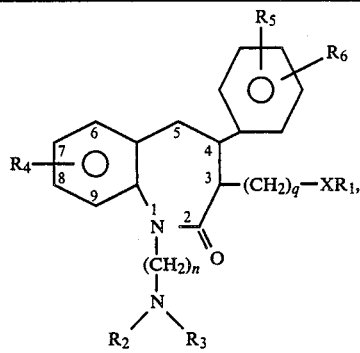

| Ex. No. | X | $R_1$ | $R_2$ | $R_3$ | $R_4$ | $R_5$ | $R_6$ | q |
|---|---|---|---|---|---|---|---|---|
| 26 | — | $\text{N}(CH_3)_2$ | $-C_2H_5$ | $-C_2H_5$ | 7-$CF_3$ | 4-$OCH_3$ | H | 2 |
| 27 | O | $-\overset{O}{\underset{\|}{C}}-CH_3$ | 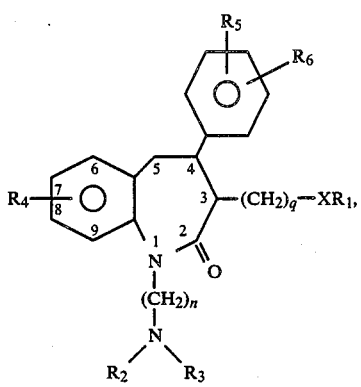 | $-CH_3$ | 6-$CF_3$ | 4-$OCH_3$ | H | 1 |
| 28 | O | $-\overset{O}{\underset{\|}{C}}-CH_3$ | $-CH_2-\text{Ph}$ | $-CH_3$ | 7-$CF_3$ | 4-$OCH_3$ | H | 1 |

What is claimed is:

1. A compound having the formula

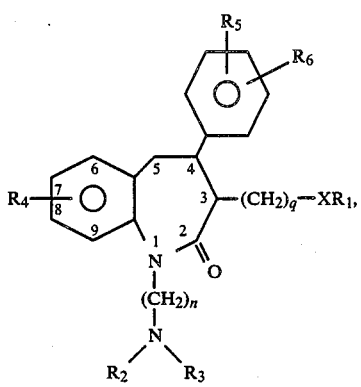

including pharmaceutically acceptable salts thereof, wherein $R_1$ is alkyl, acetyl, aryl, arylalkyl, or $-NR_7R_8$;

X is oxygen or sulfur, or, is a single bond when $R_1$ is $-NR_7R_8$;

$R_2$ and $R_3$ are each independently hydrogen, alkyl, cycloalkyl or arylalkyl, or $R_2$ and $R_3$ together with the nitrogen atom to which they are attached are pyrrolidinyl, piperidinyl, or morpholinyl;

$R_4$, $R_5$ and $R_6$ are each independently hydrogen, halogen, alkyl, alkoxy, aryloxy, arylalkoxy, diarylalkoxy, arylalkyl, cyano, hydroxy, alkanoyloxy,

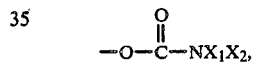

fluoro substituted alkoxy, fluoro substituted alkyl, (cycloalkyl)-alkoxy, $-NO_2$, $-NX_3X_4$, $-S(O)_m$alkyl, $-S(O)_m$aryl,

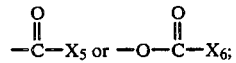

$R_7$ and $R_8$ are each independently hydrogen, alkyl, cycloalkyl or arylalkyl, or $R_7$ and $R_8$ together with the nitrogen atom to which they are attached are pyrrolidinyl, piperidinyl or morpholinyl;

n is 2 or 3;

m is 0, 1 or 2;

q is an integer from 1 to 5;

$X_1$ and $X_2$ are each independently hydrogen, alkyl, aryl or heteroaryl, or $X_1$ and $X_2$ together with the nitrogen atom to which they are attached are pyrrolidinyl, piperidinyl or morpholinyl;

$X_3$ and $X_4$ are each independently hydrogen, alkyl, alkanoyl, arylcarbonyl, heteroarylcarbonyl, or

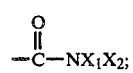

$X_5$ is hydroxy, alkoxy, aryloxy, amino, alkylamino or dialkylamino; and $X_6$ is alkyl, alkoxy or aryloxy; with the proviso that if $R_4$ is a 7-alkyl group, it must have a tertiary carbon atom bonded to the ring; and further wherein the terms "alkyl" and "alkoxy", by themselves or as part of another group, refer to both straight and branched chain groups having 1 to 10 carbon atoms;

the term "alkenyl", by itself or as part of another group, refers to both straight and branched chain groups having 2 to 10 carbon atoms;

the term "aryl", by itself or as part of another group, refers to phenyl and phenyl substituted with 1, 2 or 3 groups independently selected from amino, alkylamino, dialkylamino, nitro, halogen, hydroxyl, trifluoromethyl, alkyl of 1 to 4 carbon atoms, alkoxy of 1 to 4 carbon atoms, alkanoyloxy, carbamoyl, or carboxyl;

the term "alkanoyl", by itself or as part of another group, refers to groups having the formula

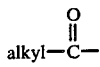

having 2 to 11 carbon atoms; the term "heteroaryl" refers to pyridinyl, pyrrolyl, imidazolyl, furyl, thienyl and thiazolyl;

the term "cycloalkyl" refers to groups having 3, 4, 5, 6 or 7 carbon atoms; and, the terms "fluoro substituted alkyl" and "fluoro substituted alkoxy", by themselves or as part of another group, refer to said alkyl and said alkoxy groups in which one or more hydrogens have been replaced by fluorine atoms.

2. A compound of claim 1 wherein
$R_1$ is methyl or $-NR_6R_7$;
$R_2$ and $R_3$ are each methyl or $R_2$ is hydrogen and $R_3$ is methyl;
$R_4$ is trifluoromethyl;
$R_5$ is 4-methoxy;
$R_6$ is hydrogen;
$R_7$ and $R_8$ are each methyl; and,
q is 1 or 2.

3. A compound of claim 1 wherein
X is oxygen;
$R_1$ is methyl;
$R_2$ and $R_3$ are each methyl;
$R_4$ is 7-trifluoromethyl;
$R_5$ is 4-methoxy;
$R_6$ is hydrogen; and, q is 1.

4. A compound of claim 1 wherein
X is sulfur;
$R_1$ is methyl;
$R_2$ and $R_3$ are each methyl;
$R_4$ is 7-trifluoromethyl;
$R_5$ is 4-methoxy;
$R_6$ is hydrogen; and,
q is 1.

5. A compound of claim 1 wherein
X is a single bond;
$R_1$ is

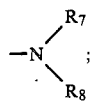

$R_2$ and $R_3$ are each methyl;
$R_4$ is 7-trifluoromethyl;
$R_5$ is 4-methoxy;
$R_6$ is hydrogen;
$R_7$ and $R_8$ are each methyl; and,
q is 1.

6. A compound of claim 1 wherein
X is oxygen;
$R_1$ is acetyl;
$R_2$ and $R_3$ are each methyl;
$R_4$ is 7-trifluoromethyl;
$R_5$ is 4-methoxy;
$R_6$ is hydrogen; and,
q is 2.

7. A compound of claim 1 having the name cis)-1-[2-(dimethylamino)ethyl]-1,3,4,5-tetrahydro-3-(methoxymethyl)-4-(4-methoxyphenyl)-7-(trifluoromethyl)-2H-1-benzazepin-2-one, fumarate (1:1) salt.

8. A compound of claim 1 having the name (cis)-1-[2-(dimethylamino)ethyl]-1,3,4,5-tetrahydro-4-(4-methoxyphenyl)-3-[(methylthio)methyl]-7-(trifluoromethyl)-2H-1-benzazepin-2-one, fumarate (1:1) salt.

9. A compound of claim 1 having the name (cis)-3-[2-(acetyloxy)ethyl]-1-[2-(dimethylamino)ethyl]-1,3,4,5-tetrahydro-4-(4-methoxyphenyl)-7-(trifluoromethyl)-2H-1-benzazepin-2-one, monohydrochloride.

10. A compound of claim 1 having the name (cis)-1-[2-(dimethylamino)ethyl]-3-[(dimethylamino)methyl]-1,3,4,5-tetrahydro-4-(4-methoxyphenyl)-7-(trifluoromethyl)-2H-1-benzazepin-2-one, fumarate (1:2) salt.

11. A composition useful in reducing blood pressure comprising a pharmaceutically acceptable carrier and an anti-hypertensively effective amount of a compound or pharmaceutically acceptable salt thereof of the formula

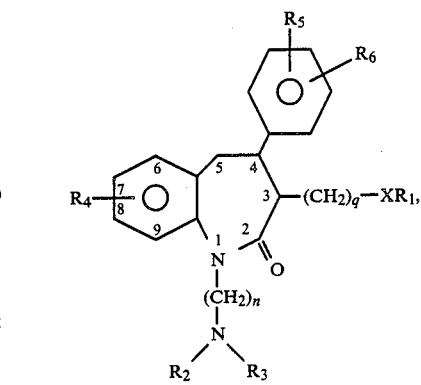

wherein X, $R_1$, $R_2$, $R_3$, $R_4$, $R_5$, $R_6$, q and n are as defined in claim 1.

12. A method of reducing blood pressure in a mammal comprising administering an effective amount of the composition of claim 11.

* * * * *

UNITED STATES PATENT AND TRADEMARK OFFICE
CERTIFICATE OF CORRECTION

PATENT NO. : 4,774,239

DATED : September 27, 1988

INVENTOR(S) : Jagabandhu Das

It is certified that error appears in the above-identified patent and that said Letters Patent is hereby corrected as shown below:

Column 7, line 25, insert --e.g., dimethylformamide, and in the presence of a base,-- after "solvent,".

Signed and Sealed this

Thirty-first Day of January, 1989

*Attest:*

DONALD J. QUIGG

*Attesting Officer*      *Commissioner of Patents and Trademarks*